US00PP25175P2

(12) United States Plant Patent
Hanes

(10) Patent No.: US PP25,175 P2
(45) Date of Patent: Dec. 16, 2014

(54) ***PELARGONIUM* PLANT NAMED 'PEQZ0006'**

(50) Latin Name: ***Pelargonium* interspecific**
Varietal Denomination: PEQZ0006

(71) Applicant: Syngenta Crop Protection AG, Basel (CH)

(72) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 57 days.

(21) Appl. No.: 13/986,616

(22) Filed: May 17, 2013

(51) Int. Cl.
*A01H 5/00* (2006.01)

(52) U.S. Cl.
USPC ..... Plt./324

(58) Field of Classification Search
USPC ..... Plt./324
See application file for complete search history.

*Primary Examiner* — Kent L Bell
(74) *Attorney, Agent, or Firm* — Joshua L. Price

(57) ABSTRACT

A new *Pelargonium* plant named 'PEQZ0006' particularly distinguished by the large brilliant semi-double red-purple flowers with a faint large-size splash pattern, fairly large inflorescences, medium green foliage without zonation, superior branching, good vigor and is tolerant of heat and drought.

1 Drawing Sheet

Latin name of the genus and species of the plant claimed: *Pelargonium* interspecific.

Varietal denomination: 'PEQZ0006'.

BACKGROUND OF THE NEW PLANT

The present invention comprises a new *Pelargonium*, botanically known as *Pelargonium* interspecific, and hereinafter referred to by the variety name 'PEQZ0006'.

'PEQZ0006' is a product of a planned breeding program. The new cultivar 'PEQZ0006' has large brilliant red-purple flowers with a faint large-size bicolor pattern, fairly large inflorescences, medium green foliage without zonation, superior branching, good vigor and is tolerant of heat and drought.

'PEQZ0006' originates from a hybrid cross made in September 2009 in a greenhouse in Gilroy, Calif. USA. The female parent was an unpatented, proprietary seedling of *Pelargonium* interspecific background, identified as '10630-1' with rose-pink bicolored flowers; that has smaller flower size with a lighter rose colored blotch, and the rose blotch is smaller , all when compared to 'PEQZ0006'.

The male parent of 'PEQZ0006' was an unpatented, proprietary seedling of *Pelargonium hortorum* background, identified as '10816-4' with rose bicolored flowers; smaller blotch size, and is less free-flowering than that of 'PEQZ0006'. The resultant seed was sown in a greenhouse in August 2010 in Gilroy, Calif.

'PEQZ0006' was selected as one flowering plant within the progeny of the stated cross in November 2010 in Gilroy, Calif.

The first act of asexual reproduction of 'PEQZ0006' was accomplished when vegetative cuttings were propagated from the initial selection in November 2010 in Gilroy, Calif.

BRIEF SUMMARY OF INVENTION

Horticultural examination of plants grown from cuttings of the plant initiated in November 2010 in Gilroy, Calif., and continuing thereafter, has demonstrated that the combination of characteristics as herein disclosed for 'PEQZ0006' are firmly fixed and are retained through successive generations of asexual reproduction.

'PEQZ0006' has not been observed under all possible environmental conditions. The phenotype may vary significantly with variations in environment such as temperature, light intensity, and day length.

A Plant Breeder's Right for this cultivar was applied for in Canada on May 24, 2012 (12-7613). 'PEQZ0006' has not been made publicly available more than one year prior to the filing of this application.

The following traits have been repeatedly observed and are determined to be basic characteristics of the new variety. The combination of these characteristics distinguishes this *Pelargonium* as a new and distinct variety

BRIEF DESCRIPTION OF THE PHOTOGRAPHS

The accompanying photographic drawing shows typical flower and foliage characteristics of 'PEQZ0006' with colors being as true as possible with an illustration of this type. The photographic drawing shows a flowering plant of the new variety.

DETAILED BOTANICAL DESCRIPTION

The plant descriptions and measurements were taken in Gilroy, Calif. in late April 2013 under natural light. The plants used were grown in a greenhouse trial and about 16 weeks of age. The plant used for the photograph was about 14 weeks with the photograph taken April 2012 in Gilroy, Calif.

Color chart used: Royal Horticultural Society Colour Chart (R.H.S.) 2001

TABLE 1

DIFFERENCES BETWEEN THE NEW VARIETY 'PEQZ0006' AND MOST SIMILAR VARIETY FOR COLOR

| | 'PEQZ0006' | 'Amri Pikegs' (U.S. Plant Pat. No. 20,481) |
|---|---|---|
| Plant habit: | More spreading | More upright |
| Flower size: | Larger | Smaller |
| Branching habit: | More branching | Less branching |
| Vigor: | More | Less |

TABLE 2

DIFFERENCES BETWEEN THE NEW VARIETY 'PEQZ0006' AND MOST SIMILAR VARIETY FOR PLANT HABIT

| | 'PEQZ0006' | 'PEQZ0002' (U.S. Plant Pat. No. 23,404) |
|---|---|---|
| Flower color: | Bicolored splash pattern | Single color |
| Flower shape: | Fuller with wider overlapping petals | Can have some gaps between petals |

Plant:

*Form, growth and habit.*—Initially semi-upright, later creeping and trailing, medium sized, well-branched.

*Plant height.*—About 15-17.0 cm.

*Plant height (inflorescence included).*—About 25-26.0 cm.

*Plant width.*—About 30-35.0 cm.

Roots:

*Number of days to initiate roots.*—15 days at about 22 degrees C.

*Number of days to produce a rooted cutting.*—20-24 days at 22 degrees C.

*Type.*—Fine, fibrous, free branching.

*Color.*—RHS N155B but whiter.

Foliage:

*Immature leaf, color upper surface.*—RHS 146A but more green.

*Immature leaf, color lower surface.*—RHS 146B.

*Mature leaf, color upper surface.*—RHS 146A.

*Mature leaf, color lower surface.*—RHS 146B.

*Length.*—4.3-5.0 cm.

*Width.*—7.0-8.2 cm.

*Shape.*—Reniform.

*Base shape.*—Cordate.

*Apex shape.*—Rounded to truncate.

*Margin.*—Crenate.

*Texture upper side.*—Hirsute.

*Texture lower side.*—Hirsute.

*Leaf zonation.*—Is not present.

*Color of veins, upper surface.*—RHS 146C.

*Color of veins, lower surface.*—RHS 146C.

*Pattern of veining.*—Palmate.

*Petiole color.*—RHS 146C.

*Petiole length.*—7-8.0 cm.

*Diameter of petiole.*—0.3 cm.

*Texture.*—Hirsute.

Stem:

*Color of stem.*—Closest to RHS 146B.

*Quantity of branches.*—3-5.

*Length of stem.*—10-12.0 cm.

*Diameter.*—0.6 cm.

*Length of internodes.*—0.5 cm.

*Texture.*—Hirsute.

Peduncle:

*Color of peduncle.*—RHS 146B to RHS 146C.

*Length of peduncle.*—11-17.0 cm.

*Peduncle diameter.*—0.4 cm.

*Texture.*—Hirsute, pilose.

Pedicel:

*Color of pedicel.*—RHS 146D becoming covered with anthocyanin of about RHS 176A.

*Length of pedicel.*—2.2-3.2 cm.

*Diameter of pedicel.*—0.15 cm.

*Texture.*—Hirsute, glandular hairs.

Bud (just before opening):

*Color.*—Closest to RHS N57A but darker.

*Length.*—1.2-1.4 cm.

*Width.*—0.6-0.8 cm.

*Shape.*—Oval.

Inflorescence:

*Type.*—An umbel, semi-spherical or nearly semi-spherical.

*Lastingness of individual flowers.*—7-9 days at 18° C. temperature.

*Number of inflorescences per plant.*—7 umbels with open flowers and 8 more with only buds.

*Fragrance.*—None.

*Umbel diameter.*—About 10-12.0 cm.

*Umbel depth.*—About 5.5 cm.

Corolla:

*Form.*—5, over-lapping petals, very wavy and ruffled appearance.

*Diameter of flower.*—3.4-4.2 cm flattened out.

*Depth of flower.*—1.0-2.0 cm.

*Color upper petals, upper surface.*—Closest to RHS N57C overlaid lightly with varying hues of RHS N57A and RHS N57B along the margins; in the center of petals, large blotch of closest to RHS 46B; and at the base, RHS 65A with longitudinal stripes and a blotch RHS 46B.

*Color upper petals, lower surface.*—Lighter than RHS N57C with veining of RHS N57B.

*Length of upper petals.*—2.5-3.0 cm.

*Width of upper petals.*—2.2-2.4 cm.

*Color lower petals, upper surface.*—Same as upper petals.

*Color lower petals, lower surface.*—Same as upper petals.

*Length of lower petals.*—2.5 cm.

*Width of lower petals.*—2.4-2.5 cm.

*Petal shape.*—Spathulate to obovate.

*Apex shape.*—Rounded.

*Margin.*—Entire.

*Base.*—Cuneate.

*Petal texture, upper surface.*—Papillose.

*Petal texture, lower surface.*—Papillose.

*Number of petaloids.*—None present.

Calyx:

*Number of sepals.*—5.

*Color of sepals.*—RHS 146C.

*Length of sepals.*—1.1-1.2 cm.

*Width of sepals.*—0.3-0.5 cm.

*Sepal shape.*—Lanceolate.

*Apex shape.*—Acute.

*Margins.*—Entire.

*Texture.*—Hirsute, glandular hairs.

Reproductive organs:

*Gynoecium*.—Pistil: 1. Length: 1.0 cm. Style color: RHS 60A. Style length: 0.3 cm. Stigma color: RHS 60A. Ovary color: RHS 141C. Ovary length: 0.4-0.5 cm. Ovary diameter: 0.15-0.2 cm.

*Androecium*.—Number of anthers: About 8; sometimes with a few extra filaments that aren't fully formed with anthers. Length of anthers: 0.15-0.2 cm. Anther color: RHS 53C. Length filaments: 0.3-0.4 cm. Color of filaments: RHS N155B with RHS 47B on the apex. Pollen amount: Normal. Color of pollen: RHS 187C. Fertility/seed set: Has not been observed to date. Disease/pest resistance: Has not been observed to date.

What is claimed is:

1. A new and distinct variety of *Pelargonium* plant named 'PEQZ0006' substantially as illustrated and described herein.

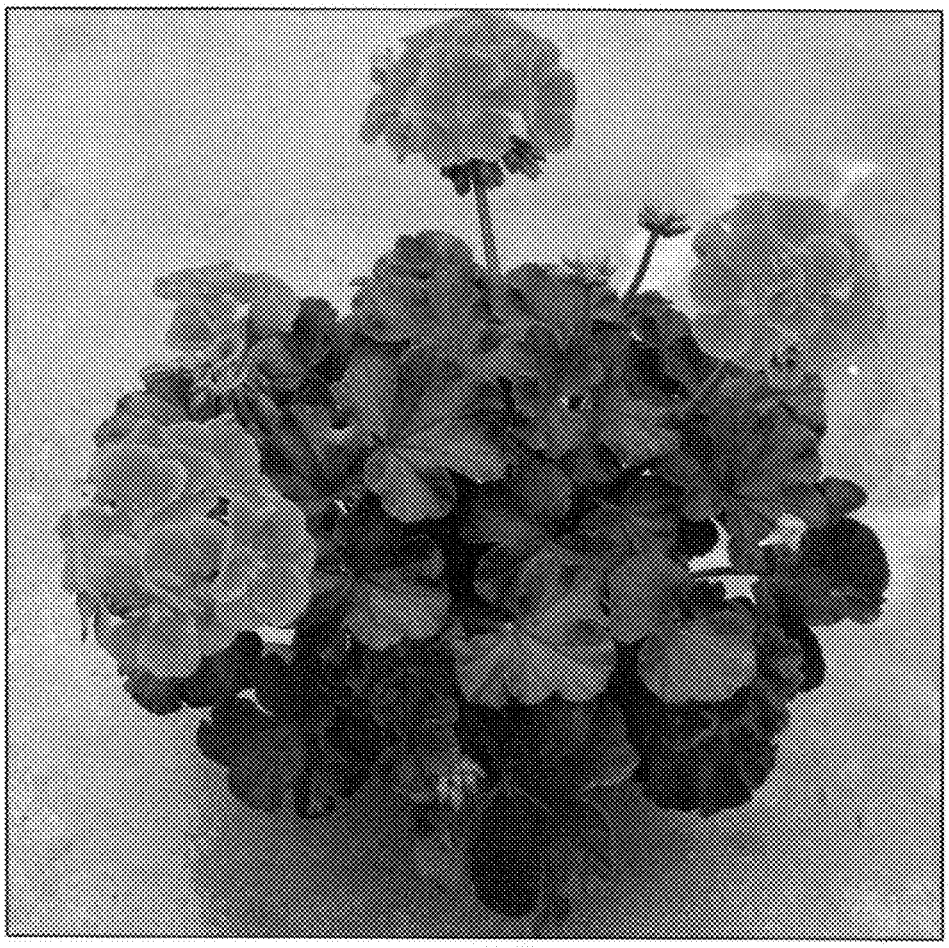

* * * * *